United States Patent [19] [11] 4,371,696
Lombardino et al. [45] Feb. 1, 1983

[54] CERTAIN PYRIDINE METHYLTHIO ACETALDEHYDE DERIVATIVES AND NON-CYCLIC AND CYCLIC ACETALS THEREOF

[75] Inventors: Joseph G. Lombardino, Niantic; Charles A. Harbert, Waterford, both of Conn.

[73] Assignee: Pfizer Inc., New York, N.Y.

[21] Appl. No.: 276,242

[22] Filed: Jun. 26, 1981

Related U.S. Application Data

[60] Continuation-in-part of Ser. No. 168,127, Jul. 14, 1980, abandoned, which is a division of Ser. No. 85,011, Oct. 15, 1979, Pat. No. 4,246,263.

[51] Int. Cl.³ .................. C07D 407/12; C07D 213/48; C07D 213/51
[52] U.S. Cl. .................. 546/283; 546/339; 546/340; 424/263
[58] Field of Search .................. 546/283, 339, 340; 424/263

[56] References Cited

FOREIGN PATENT DOCUMENTS 1213049 11/1970 United Kingdom .................. 546/341
1434271 5/1976 United Kingdom .................. 544/25

Primary Examiner—Alan L. Rotman
Attorney, Agent, or Firm—Connolly and Hutz

[57] ABSTRACT

A series of 4-(2-carboxymethylthiomethyl)pyridines and related compounds, and their pharmaceutically acceptable salts, are disclosed as having antiinflammatory and immunoregulatory activity. Preferred compounds include 4-(2-carboxymethylthiomethyl)pyridine [alternatively named 2-(4-picolylthio)acetic acid] and ($C_1$–$C_4$)alkyl esters thereof, and 4-(1-formylmethylthiomethyl)pyridine [alternatively named 2-(4-picolylthio)-acetaldehyde] and bis($C_1$–$C_4$)alkyl or cyclic acetals thereof. These acids, esters, aldehydes and acetals also have utility as intermediates in the synthesis of the corresponding 4-(2-hydroxyethylthiomethyl)pyridines.

6 Claims, No Drawings

CERTAIN PYRIDINE METHYLTHIO ACETALDEHYDE DERIVATIVES AND NON-CYCLIC AND CYCLIC ACETALS THEREOF

CROSS REFERENCE TO RELATED APPLICATIONS

This application is a continuation-in-part of copending application Ser. No. 168,127, filed July 14, 1980, now abandoned, which is a division of application Ser. No. 85,011, filed Oct. 15, 1979, now U.S. Pat. No. 4,246,263.

BACKGROUND OF THE INVENTION

This invention relates to pyridines substituted at the 4-position with a thioether and carboxy, ($C_2$–$C_5$)carboalkoxy or formyl containing side chain, and the pharmaceutically acceptable salts thereof, having utility in the treatment of arthritis as well as utility as intermediates for the preparation of the corresponding alcohols having the same utility.

A number of compounds have been known in the art to be useful as antiinflammatory agents, for example the corticosteroids, phenylbutazone, indomethacin, piroxicam and other benzothiazine dioxides (Lombardino, U.S. Pat. No. 3,591,584), 2-oxo-2,3-dihydrobenzofuran-3-carboxamides (Kadin, U.S. Pat. No. 3,676,463), and substituted diarylimidazoles (Lombardino, U.S. Pat. No. 3,707,475). Accordingly these compounds have therapeutic value in the treatment of arthritic and other inflammatory conditions. Such conditions have also been treated by administration of immunoregulatory agents, such as levamisole, as described, for example, in Arthritis and Rheumatism, 20, 1445 (1977) and Lancet, 1, 393 (1976). In efforts to find new and improved therapeutic agents for the treatment of these conditions, it has now been found that the novel pyridines of the present invention are active either as antiinflammatory agents or as regulants of the immune response in mammals, and in many cases, possess both types of activity. Because these activities are complementary, the latter are of particular value in the treatment of rheumatoid arthritis and other conditions where relief of the inflammation and regulation of the immune response is desired.

Not all of the compounds of the present invention are novel. Thus, acids and esters of the formula (I) wherein n=1 and Z=hydroxy or ($C_1$–$C_4$)alkoxy have been disclosed as compounds useful as intermediates in the preparation of cephalosporin derivatives, British Patent Specification No. 1,434,271 (1976); specifically described are 2-(4-picolylthio)acetic acid and methyl 2-(4-picolylthio)acetate. Isomeric 2-(3-carboxypropylthiomethyl)pyridine and the corresponding alkyl ester derivatives have also been reported (British Patent Specification No. 1,213,049); the latter compounds are claimed to be useful for treating inflammation in non-human animals, but may well be devoid of the desirable immunoregulatory activity of the present compounds, since the derived alcohols are devoid of such activity at a level where alcohols derived from the present compounds have a high level of activity.

SUMMARY OF THE INVENTION

In accordance with the present invention, it has been unexpectedly found that certain novel pyridine derivatives, together with their pharmaceutically acceptable salts, are useful when used therapeutically as either antiinflammatory agents or as regulators of the immune response. They are particularly useful in conditions such as rheumatoid arthritis where both antiinflammatory and immunoregulatory agents have been used individually for therapeutic purposes.

The therapeutic agents of this invention are of the formula

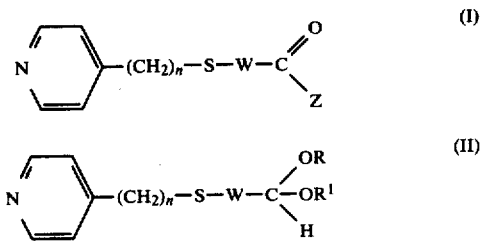

wherein
n is an integer of value 1 or 2;
W is methylene, unsubstituted or substituted with either a methyl or a phenyl group;
Z is hydroxy, ($C_1$–$C_4$)alkoxy, or hydrogen;
R and $R^1$ when taken separately are the same and are each ($C_1$–$C_4$)alkyl; and
R and $R^1$ when taken together are ethano (—$CH_2CH_2$—) or propano (—$CH_2CH_2CH_2$—);
the pharmaceutically acceptable acid addition salts thereof; and
the pharmaceutically acceptable cationic salts thereof when Z is hydroxy.

Preferred among these compounds are the pyridines of the formula (I) and (II) wherein n is 1; most preferred further have W as unsubstitituted methylene.

Antiinflammatory activity is reflected in the so-called rat foot edema test, in which the ability of an oral dose of the compound to inhibit an inflammatory reaction is measured, while immunoregulatory activity is assessed by the so-called mouse E-rosette procedure in which the ability of the test compound to restore erythrocyte rosette formation in thymectomized mice is measured. These tests are described in greater detail below.

This invention also encompasses pharmaceutical compositions of the above enumerated pyridine derivatives, as well as their use as antiinflammatory and immunoregulatory agents, particularly in the therapy of arthritis.

DETAILED DESCRIPTION OF THE INVENTION

Convenient methods are available for the preparation of the pyridine-acids, esters and aldehydes of the present invention. The methods are enumerated as follows:

(1) Reaction of 4-picolylmercaptan or 2-(4-pyridyl)ethyl mercaptan with an alpha-haloacid, ester, aldehyde or acetal, followed, if desired, by suitable hydrolysis, esterification or acetalization. For example:

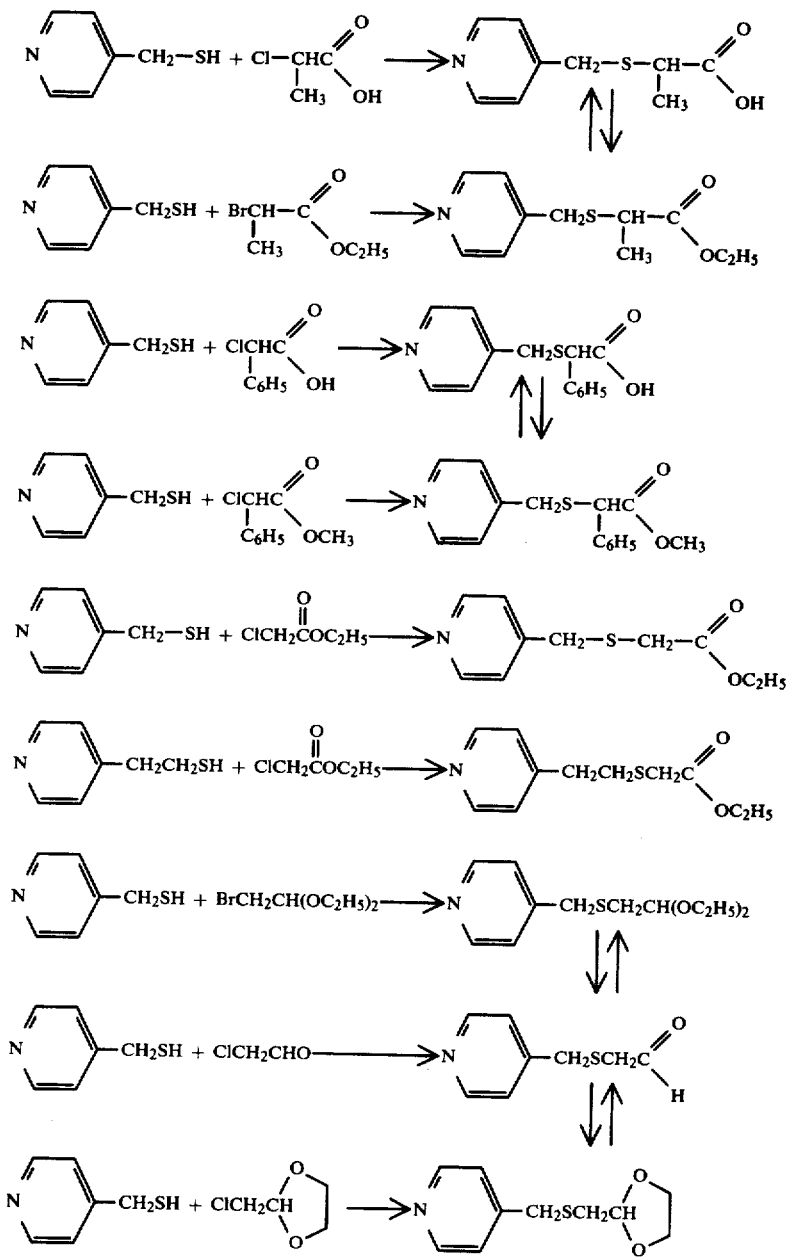
(2) The reaction of 4-picolyl halide or 2-(4-pyridyl)-ethyl halide with a suitable substituted mercaptan (cf. method 1 above), followed, if desired, by suitable hydrolysis, esterification or acetalization. For example:
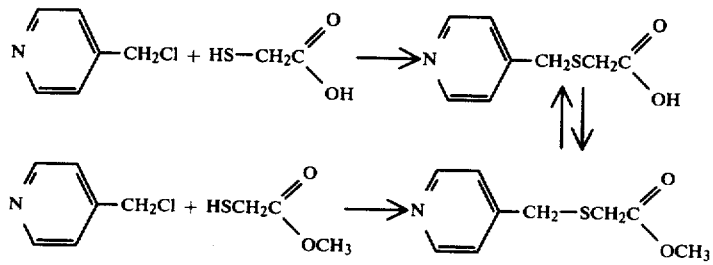

-continued

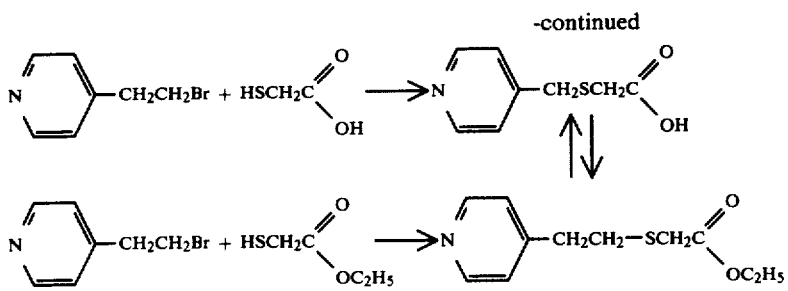

(3) Addition of mercaptoesters to 4-vinylpyridine, followed, if desired, by hydrolysis. For example:

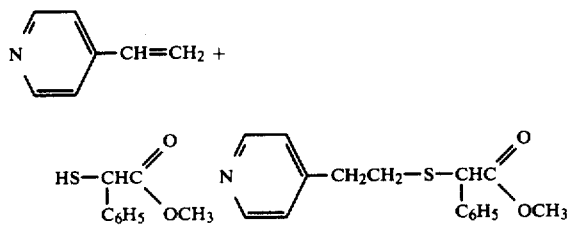

The displacement methods (1) and (2) involve a reaction in which the halogen of an organic halide is replaced by an organic thio residue. The reaction is facilitated by using an equivalent of strong base to convert the mercaptan to anionic salt, which is much more efficient in converting the organic halogen to the thio ether. When an acid salt of the pyridine moiety (e.g. 4-picolyl chloride hydrochloride) or an acid (e.g. alpha-mercaptopropionic acid) is employed as one of the reactants, a compensating amount of base is added. A wide variety of solvents are suitable for this reaction, including alcohols, acetonitrile, dimethylformamide, etc., the only requirement being that the solvent be inert towards reactants and product, and that the reactants have some degree of solubility. Preferably, the solvent should be less acidic than the mercaptan, so as to facilitate formation of the thio anion. The temperature employed for this reaction is not critical (e.g. 0°–120° C.). It should be high enough to provide a reasonable rate, but not so high as to lead to undue decomposition. As is well known in the art, rate will vary with the nature of the organic halide (rate: I>Br>Cl), the structure of both the halide and the mercaptan, and the solvent. The reaction time should be such that the reaction is nearly complete (e.g. >95% conversion when equivalent amounts of halide and mercaptan are employed) to maximize yields (e.g. 1 hour to several days). These reactions are readily monitored by thin layer chromatography, employing one of a variety of commercially available silica gel plates containing an ultraviolet indicator. Suitable eluants are chloroform/methanol mixtures with the proportion of these solvents varied with the polarity of the reaction product, a practice well-known in the art. For most of the reactions of this type, an eluant consisting of 9 parts of chloroform and 1 part of methanol is well suited. For the more polar compounds the proportion of methanol is increased (e.g. 4 chloroform/1 methanol). It is sometimes advantageous to add up to 5% acetic acid to the eluant, particularly when dealing with acid addition salts. Ethyl acetate and other alcohols (e.g. butanol) as well as a proportion of water can also be employed in the eluant. As the reaction proceeds, an equivalent of strong acid is produced, neutralizing the mole of base used in the reaction. For this reason pH can also be used as an aid in monitoring this reaction.

The method (3), addition of mercaptans to 4-vinylpyridine is carried out under conditions of temperature and solvent which correspond to those for the replacement of organic halogen by organic thio radical as discussed above. In this case also, suitable reaction times can be determined by use of the same thin layer chromatography systems.

Hydrolysis of the esters and acetals of methods (1) to (3) is carried out under standard conditions, well known in the art. For example, water, optionally diluted with a miscible organic solvent, and an acid catalyst (for either acetal or ester hydrolysis) or base catalyst (only in the case of ester hydrolysis) at ambient temperature for a few hours up to a day or more are convenient conditions employed for these reactions.

Acetalization and esterification of aldehydes and acids, respectively, are also carried out under standard conditions well known in the art. Typically, excess of the anhydrous alcohol or bis-alcohol is employed as solvent, together with an acid catalyst, such as p-toluenesulfonic acid or a strong acid ion exchange resin. Ambient temperature will generally be employed, since temperature is not critical, for from a few hours up to a day or more so as to permit reaction to be substantially complete.

The starting materials required for methods (1)–(3) are quite generally available from the literature or commercially. Mercaptans can be prepared from the corresponding halides by reaction of the halide with thiourea to form the isothiuronium salt followed by basic hydrolysis (see Preparations 1 and 2 below), by reaction of organic halides with hydrogen sulfide or alkali metal hydrosulfide [e.g. Hromatka et al., Monatsh. 78, 32 (1948)], or both hydrolysis of thiol esters [e.g. Chapman et al., J. Chem. Soc., 579 (1950); Sjoberg, Ber. 75, 13 (1942); von Wacek et al., Ber. 75, 1353 (1942)]. Organic halides required as starting materials are also generally available commercially or in the literature. Typical methods for making the required halides are direct halogenation, or the action of hydrogen or phosphorous halides on an alcohol.

The pharmaceutically acceptable acid addition salts of the novel pyridines of the present invention are readily prepared by contacting the free base with the appropriate mineral or organic acid in either aqueous solution or in a suitable organic solvent. The salt can then be obtained by precipitation or by evaporation of the solvent. The pharmaceutically acceptable acid addition salts of this invention include, but are not limited to, those formed with hydrochloric, hydrobromic, hitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred. If desired, these salts are isolated directly from reaction mixtures by suitable modification of the isolation procedure, without isolation of the intermediate free acid.

The pharmaceutically-acceptable cationic salts of the compounds of the present invention are readily prepared by reacting the acid forms with an appropriate base, usually one equivalent, in a co-solvent. By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine (N-benzylphenethylamine), diethylamine, piperazine, and tromethamine (2-amino-2-hydroxymethyl-1,3-propanediol). Typical bases employed in the preparation of these cationic salts are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a nonsolvent. In some cases, salts can be prepared by mixing a solution of the acid with a solution of a different salt of the cation (e.g., sodium ethylhexanoate, magnesium oleate), employing a solvent in which the desired cationic salt precipitates, or can be otherwise isolated by concentration and/or addition of a non-solvent. If desired, these salts are isolated directly from the reaction mixtures by suitable isolation procedures, without isolation of the intermediate free acid.

The utility of the present compounds in the synthesis of immunoregulatory, antiinflammatory pyridine-alcohols is set forth in related U.S. Pat. No. 4,246,263, referenced above.

The immunoregulatory activity of the compounds of this invention is assessed by the mouse E-rosette procedure. In the mouse, the presence of a thymus is required for full expression of normal rosette formation with sheep erythrocytes [see for example, Bach and Dardenne, Immunol. 25, 353 (1973)]. The procedure examines the ability of a drug to restore azathioprine-sensitive, rosette-forming cells in adult thymectomized mice to the levels of normal animals. Specifically, rosette formation is examined in CD-1 mice thymectomized at 4 weeks of age and left at least 14 days post-surgery before manipulation (ATX mice). The ATX mice are dosed orally either with saline vehicle or drug. Sixteen hours later, single cell suspensions are prepared in Hanks balanced salt solution (HBSS) from the pooled spleens of three mice. To each tube is added 0.1 ml of lymphocytes ($6 \times 10^7$/ml) in HBSS and either 0.1 ml of HBSS or 0.1 ml of 40 μg/ml azathioprine in HBSS. After 90 minutes incubation at 37° C., the cells are washed 2× with 5 ml. of HBSS, made back up to 0.2 ml, and 0.2 ml of sheep red blood cells (erythrocytes) at $1.2 \times 10^8$ cells/ml. added. Then μl are pipetted on hemagglutination slides and the number of rosettes counted. The ability of the test compound to restore the number of azathioprine sensitive rosetting cells to normal or higher is determined. In normal mice 42% ± 12% aza- thioprine sensitivity is found. In adult thymectomized mice 3 ± 3% azathioprine sensitivity is found. Typical of the ability of the compounds of the present invention to restore azathioprine sensitive rosetting cells to normal or above at various oral dosages (mg./kg., i.e. mg. of drug/kg. of mouse body weight) is the immunoregulatory activity of 2-(4-picolylthio)acetic acid shown in Table I. The higher the percentage and the lower the effective dosage, the more active is the compound as an immunoregulatory agent.

TABLE I

Immunoregulatory Activity
Activity of 2-(4-Picolylthio)acetic Acid
in the Mouse E-Rosetting Procedure

| Oral Dosage | % Rosetting Cells |
|---|---|
| 0.1 | 15 |
| 0.3 | 15 |
| 1.0 | 35, 40 |
| 3.0 | 40 |

The antiinflammatory activity of the compounds of the present invention is determined in the standard carrageenin-induced rat foot edema test [described by C. A. Winter et al., Proc. Soc. Exp. Biol. 111, p. 544 (1962)]. In this test, antiinflammatory activity is determined as the inhibition of edema formation in the hind paw of male albino rats (weight 150–190 g.) in response to a subplantar injection of carrageenin. The carrageenin is injected as a 1 percent aqueous suspension (0.05 ml.) 1 hour after oral administration of the drug. Edema formation is then assessed 3 hours after the carrageenin injection by measuring the volume of the injected paw initially as well as at the 3 hour mark. The increase in volume three hours after carrageenin injection constitutes the individual response. Compounds are considered active if the response between the drug-treated animals (six rats/group) and the control group (i.e., animals receiving the vehicle alone) is deemed to be significant on comparison with results afforded by standard compounds like acetylsalicylic acid at 100 mg./kg or phenylbutazone at 33 mg./kg., both by the oral route of administration. The activity of the compound under test is expressed as the % inhibition of edema at a given oral dose.

The novel pyridines of this invention and their pharmaceutically acceptable salts are useful therapeutically as antiinflammatory agents or as regulants of the immune response in warm-blooded animals. The combination of antiinflammatory activity and immune regulant activity is particularly valuable in the treatment of conditions such as rheumatoid arthritis and other diseases associated with immune deficiency and accompanied by inflammation. Thus, compounds of the present invention act to relieve the pain and swelling associated with such conditions while also regulating the immune response of the subject and thereby alleviating the underlying immune disorder by maintaining immune competence. Accordingly, the present invention embraces a method of inhibiting inflammatory reactions or regulating the immune response in a warm-blooded animal by administering to the subject a pyridine of the present invention, or a pharmaceutically acceptable acid addition salt thereof, in an amount sufficient to inhibit the inflammatory reactions or regulate the immune response. In accord with this method, the compounds of the present invention are administered to the subject in need of treatment by conventional routes, such as orally or parenterally, at dosages in the range of about 0.25 to about 100 mg./kg. body weight of the subject per day, preferably about 0.25 to about 50 mg./kg. body weight per day administered singly or as a divided dose. However, the optimum dosage for the individual subject being treated will be determined by the person responsible for treatment, generally smaller doses being administered initially and thereafter gradual increments made to determine the most suitable dosage. This will vary according to the particular compound employed and with the subject being treated.

The compounds can be used in pharmaceutical preparations containing the compound, or a pharmaceutically acceptable salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like are used, as well as aqueous solutions of water-soluble pharmaceutically acceptable acid addition salts of the compounds. The injectable solutions prepared in this manner are administered intravenously, intraperitoneally, subcutaneously or intramuscularly, with intravenous and intramuscular administration being preferred. For localized treatment of inflammation the compounds are also administered topically in the form of ointments, creams, pastes and the like in accord with conventional pharmaceutical practice.

The present invention is illustrated by the following examples. However, it should be understood that the invention is not limited to the specific details of these examples.

EXAMPLE 1

Methyl 2-(4-picolylthio)acetate

Sodium methoxide (2.16 g., 40 mmoles) is dissolved in 24 ml. of methanol, stirring under nitrogen, and the solution cooled in an ice bath. 4-Picolyl chloride hydrochloride (3.38 g., 20 mmoles), finely divided and suspended in approximately 20 ml. of methanol, is added dropwise over approximately 15 minutes. A solution of methyl 2-mercaptoacetate (2.12 g., 20 mmoles) in 4 ml. of methanol is then added over approximately 5 minutes. The reaction mixture is warmed slowly and left to stir under nitrogen for 14 hours at room temperature. The reaction is filtered with diatomaceous earth. Solids are repulped with an additional 75 ml. of methanol. The methanol filtrates are combined and concentrated to yield title product.

Alternatively, the title product is prepared and isolated as the hydrochloride salt according to the method of British patent specification No. 1,434,271.

Furthermore 4-picolyl chloride hydrochloride or 4-picolyl bromide hydrobromide is converted to the free base by rendering the salt basic in ethanol, and then reacting with sodium or potassium cyanide (1.05 equivalents) to form the corresponding nitrile. The nitrile is solvolized in ethanol with aqueous hydrochloride acid to form ethyl 4-picolylacetate [cf. Rising et al., J. Am. Chem. Soc. 50, 1211 (1928)]. The latter is reduced with Red-al in benzene-tetrahydrofuran and isolated by the method of Examples 9 and 10, yielding 2-(4-pyridyl)ethanol. The alcohol is converted to corresponding chloride by reaction with thionyl chloride in refluxing methylene chloride [cf. Gilman et al., Rec. trav. chim. 51, 93 (1932)]. The 2-(4-pyridyl)ethyl chloride hydrochloride which forms is isolated by evaporation.

Using the above procedure 2-(4-pyridyl)ethyl chloride is reacted with methyl 2-mercaptoacetate to yield methyl 2-[2-(4-pyridyl)ethylthio]acetate.

EXAMPLE 2

Ethyl 2-(4-Picolylthio)acetate

Under nitrogen, absolute ethanol (120 ml.) was warmed to 40° C. Sodium metal (5.18 g., 0.225 mole) was added portionwise at such a rate as to maintain gentle reflux. After one hour, the resulting clear solution of sodium ethoxide was cooled in an ice-water bath. 4-Picolyl chloride hydrochloride (16.4 g., 0.10 mole) was slurried in 60 ml. of ethanol and ethyl mercaptoacetate (13.2 g., 0.11 mole) in 30 ml. of ethanol were placed in separate additional funnels. After 10% of the organic chloride was added, the remaining chloride and the mercaptan were added simultaneously and dropwise. The reaction mixture was warmed to room temperature, stirred for 16 hours and filtered over diatomaceous earth with ethanol wash. The combined filtrate and wash was evaporated to an oil (26 g.). The oil was chromatographed on 500 g. of silica gel, eluting with chloroform and monitoring by tlc. Clean fractions were combined and evaporated to yield title product as an oil [16.4 g.; $R_f$ (9:1 chloroform:methanol) 0.75; ir (film) 3390, 2976, 1730, 1600, 1410, 1280, 1160, 1120, 1030, 813, 750 cm$^{-1}$].

EXAMPLE 3

Sodium 2-(4-Picolylthio)acetate

Title ester of the preceding Example (8.0 g., 0.038 mole) was dissolved in 77 ml. of ethanol. 1 N sodium hydroxide (38 ml.) was added and the mixture stirred 48 hours at room temperature. The mixture was evaporated to dryness *in vacuo* and the residue chased with fresh ethanol and pumped under high vacuum to yield title product [6.8 g.; m.p. 158°-160°; $R_f$(90:5:5 chloroform:methanol:acetic acid) 0.25].

The same product is obtained by substituting an equivalent of the methyl ester for the ethyl ester. The acid form, 2-(4-picolyl)acetic acid, is obtained from hydrolysis of either methyl or ethyl ester according to British patent specification No. 1,434,271.

EXAMPLE 4

Sodium 2-(4-Picolylthio)propionate

Sodium methoxide (5.1 g., 94 mmoles) was dissolved in 50 ml. of absolute ethanol and cooled in an ice bath. A slurry of 4-picolyl chloride hydrochloride (5.0 g., 30.4 mmoles) in 45 ml. of ethanol was added and the chilled reaction mixture stirred for approximately 10 minutes. Finally, 2-mercaptopropionic acid (3.23 g., 30.4 mmoles) dissolved in 5 ml. of ethanol was added over a 10 minute period. The mixture was allowed to warm to room temperature and stirred overnight (approximately 16 hours). The reaction was filtered through filter aid to remove salts, carbon treated and concentrated to crude sodium 2-(4-picolylthio)propionate (approximately 7 g. of oil used directly in the next step).

EXAMPLE 5

Sodium Phenyl(4-picolylthio)acetate

Sodium methoxide (6.8 g., 0.124 mole) was dissolved in 150 ml. of ethanol and cooled to 0° C. A solution of alpha-mercaptophenylacetic acid (7.0 g., 0.042 moles) in 50 ml. of ethanol was added over a period of 5 minutes to the cold methoxide solution. After 5 minutes, a slurry of 4-picolylchloride hydrochloride (6.83 g., 0.042 moles) slurried in 50 ml. of ethanol was then added over 5 minutes. The reaction was removed from the ice bath and left to stir for approximately 60 hours. The reaction mixture was filtered and evaporated to yield sodium phenyl(4-picolylthio)acetate (11.8 g.; waxy solid; ir: 3.0, 6.1, 6.25, 7.3, 13.6$\mu$) used directly in the next step.

By the method of Examples 4 and 5, 4-picolyl chloride hydrochloride is reacted with mercaptoacetic acid to yield sodium 2-(4-picolylthio)acetate.

EXAMPLE 6

Ethyl 2-(4-Picolylthio)propionate

Crude sodium 2-(4-picolylthio)propionate (approximately 7 g.) was taken up in 100 ml. of absolute ethanol and approximately 5 cc. of 3 A molecular sieves were added. Dry hydrogen chloride was bubbled into the reaction mixture, which was refluxed for 75 minutes, while continuing to saturate with hydrogen chloride during the initial 15 minutes. The mixture was cooled to room temperature and allowed to stir overnight (approximately 16 hours). The mixture was filtered through diatomaceous earth and concentrated to a semi-solid mixture. The esterification step was repeated on this mixture, except saturation with hydrogen chloride was continued during 1 hour of reflux and refluxing was continued overnight. The reaction mixture was cooled to room temperature, filtered through diatomaceous earth and evaporated to an oil. The oil was extracted with chloroform, leaving filterable salts behind, and the chloroform stripped to yield ethyl 2-(4-picolylthio)propionate (waxy solid; ir (KBr) 3.0, 3.5, 5.75, 6.15, 6.30, 6.70, 8.6, 12.25$\mu$; m.s.: m/e calcd: 225; found: 225, 152, 124, 102, 92, 45).

Using the same ethanolic hydrogen chloride procedure, sodium 2-(4-picolylthio)acetate is converted to ethyl 2-(4-picolylthio)acetate.

EXAMPLE 7

Methyl 2-Phenyl-2-(4-picolylthio)acetate

Sodium 2-phenyl-2-(4-picolylthio)acetate was dissolved in methanol and dry hydrogen chloride added slowly so as to maintain gentle reflux for 1 hour. After cooling and stirring for approximately 16 hours, the reaction mixture was filtered and concentrated to yield title product (11.6 g.; oil; ms, calcd.: m/e 273; found: 273, 214, 150, 136, 124, 121, 105, 77, 65).

The corresponding ethyl and propyl esters are prepared by the same method, substituting ethanol and propanol, respectively, for methanol.

By the same method, sodium 2-(4-picolylthio)acetate is converted to methyl 2-(4-picolylthio)acetate.

EXAMPLE 8

4-(2,2-Diethoxyethylthiomethyl)pyridine

Under a nitrogen atmosphere, sodium methoxide (0.60 g., 11 moles) is dissolved in approximately 15 ml. of stirring ethanol and cooled in an ice bath. 4-Picolyl mercaptan (1.4 g., 11 mmoles) in approximately 3 ml. of absolute ethanol is added over 5 minutes and the mixture stirred for 15 minutes. Bromoacetaldehyde diethylacetal (2.4 g., 11 mmoles) in approximately 15 ml. of absolute ethanol is then added over 5 minutes. The reaction mixture is warmed to room temperature and stirred for 16 hours. The reaction mixture is filtered and the filtrate evaporated to yield title product, which if desired, can be further purified by chromatography on silica gel.

The title acetal is also prepared from ethanol and 2-(4-picolylthio)acetaldehyde of the next Example using the procedure of Example 6.

By the same method the ethylene glycol acetal of bromoacetaldehyde is reacted with 4-picolyl mercaptan to yield the corresponding ethylene glycol acetal of 2-(4-picolylthio)acetaldehyde.

EXAMPLE 9

2-(4-Picolylthio)acetaldehyde

By the method of the preceding Example, chloroacetaldehyde is reacted with 4-picolyl mercaptan to yield title product.

Alternatively, the same title product is obtained by hydrolysis of either one of the acetals of the preceding Example using the method of Example 3.

EXAMPLE 10

Methyl 2-[2-(4-Pyridyl)ethylthio]acetate

Under a nitrogen atmosphere, sodium methoxide (1.62 g., 0.03 mole) is dissolved in 36 ml. of stirring methanol and the solution cooled in an ice bath. Methyl 2-mercaptoacetate (3.18 g., 0.03 mole) in 6 ml. of methanol is added over approximately 5 minutes. Finally, 4-vinylpyridine (3.22 g., 0.03 mole) in approximately 20 ml. of absolute ethanol is added over 15 minutes. The reaction mixture is allowed to warm to room temperature and stirred for 23 hours. The reaction mixture is concentrated to dryness *in vacuo*. The residue is added slowly to a stirred mixture of water and chloroform. The chloroform phase is separated and the aqueous phase further extracted with chloroform. The combined chloroform phases are extracted with saturated sodium chloride, dried over anhydrous sodium sulfate, and stripped to yield title product.

EXAMPLE 11

Capsules

A dry solid pharmaceutical composition is prepared by blending the following materials together in the proportions by weight indicated below:

Methyl 2-(4-picolylthio)acetate hydrochloride—12
Calcium carbonate—20
Polyethylene glycol, average molecular weight, 4000—72

The dried solid mixture so prepared is then thoroughly agitated so as to obtain a uniform powder. Soft elastic gelatin capsules containing this pharmaceutical composition are then prepared in potencies (eqivalent to weight of free base) of 12.5 mg., 25 mg. and 50 mg. by filling with an appropriate amount of the uniform powder.

For higher potency capsules, e.g. 100 mg. capsules, a lower proportion of the inert ingredients is employed in preparation of the uniform powder for encapsulation.

To make hard gelatin filled capsules, the amount of inert ingredients is adjusted so as to conveniently fill standard sized gelatin capsules with the desired drug potency.

Alternative blends for encapsulation are prepared from lactose and cornstarch in a proportion 33 to 1 to 10 to 1, with small portion of talc if desired, combined with active ingredient sufficient to provide potencies as above when filled into capsules.

EXAMPLE 12

Tablets

A dry solid pharmaceutical composition is prepared by blending the following materials together in the proportions by weight specified below:

Methyl 2-(4-picolylthio)acetate hydrochloride—30
Sodium citrate—37.5
Alginic acid—15
Polyvinylpyrrolidone—15
Magnesium stearate—7.5

After thorough blending, tablets are punched from the resulting mixture, said tablets containing 25 mg. or 50 mg. (as weight equivalent to the free base) of the active ingredient. In a like manner, with variation in the proportion of inert ingredients if desired, tablets of 5 mg., 10 mg., 75 mg. and 100 mg. potency are also prepared.

An alternative tablet base is prepared by blending the following ingredients:

Methyl 2-(4-picolylthio)acetate hydrochloride—30
Sucrose, U.S.P.—55
Tapioca starch—15
Magnesium stearate—6.5

Tablets of the desired potency are then punched from this blend.

PREPARATION 1

4-Picolylisothiouronium chloride hydrochloride

Thiourea (11.42 g., 0.15 moles) was suspended with stirring in 45 ml. of absolute ethanol. The suspension was heated to reflux under nitrogen and a suspension of finely divided 4-picolyl chloride hydrochloride (25.37 g., 0.15 moles) in approximately 100 ml. of absolute ethanol was added over 15 minutes, with external heating removed as necessary to avoid overly vigorous reflux. After 6 hours additional reflux, the reaction mixture was cooled to room temperature and filtered, with cold ethanol wash, to yield 4-picolylisothiouronium chloride hydrochloride (35.8 g.; m.p. 226°-227° C. (dec.); ir (KBr): 3.40, 6.05, 6.14, 6.27, 6.71 and 12.34μ).

Analysis: Calcd. for C7H9N3S.2HCl: C, 35.01; H, 4.62; N, 17.50. Found: C, 35.04, H, 4.61; N, 17.55.

The same method is used to convert 2-(4-pyridyl)ethyl chloride to 2-(4-pyridyl)ethylisothiouronium chloride.

PREPARATION 2

4-Picolyl Mercaptan

4-Picolylisothiouronium chloride hydrochloride (32.4 g., 0.135 moles) was dissolved in 45 ml. of water with stirring, a warm solution of sodium hydroxide (11.02 g., 0.27 mole) in 18 ml. of water was added dropwise over approximately 10 minutes during which oil droplets began to form. The mildly exothermic reaction was allowed to stir for approximately 30 minutes, at which time the pH was increased from 7 to 8 by the addition of sodium. The pH was then reduced to 6 by the slow addition of 6 N hydrochloric acid. The oily product was extracted into ether (three 125 ml. portions). The combined ether extracts were dried over anhydrous sodium sulfate, and evaporated to an oil containing solids, with a potent mercaptan odor (11.18 g.). Fractional distillation gave purified 4-picolyl mercaptan (4.47 g.; b.p. 109°-104° C./15 mm.; thin layer chromatography on silica gel: Rf 0.65–0.7 when eluted with 4CHCl3/1CH3OH). This mercaptan readily forms a solid disulfide when contacted with air.

The same method is used to convert 2-(4-pyridyl)-ethylisothiouronium chloride to 2-(4-pyridyl)ethyl mercaptan.

PREPARATION 3

4-Picolyl Acetate

4-Picoline N-oxide (250 g.) was dissolved in a mixture of 2.5 l. of acetic acid and 425 ml. of acetic anhydride. The solution was slowly heated to reflux and refluxed for about 22 hours. The reaction mixture was then stripped of acetic acid and acetic anhydride and the residual oil vacuum distilled, using a 6 inch fractionation column. Material boiling at a pot temperature of 100° C. and a head temperature of 82° C. at 1.2 mm. was combined, yielding 305.9 g. of an 87:13 mixture of 4-picolyl acetate and 3-acetoxy-4-picoline.

PREPARATION 4

4-Picolyl Bromide Hydrobromide

4-Picolylacetate (300 g., 87% pure) was combined with 3.0 l. of 48% hydrobromic acid. A spontaneous exotherm occurred, the temperature rising from 26° C. to 42° C. The mixture was heated to reflux and refluxed for about 1 hour (pot temperature 124° C.). The reaction mixture was then concentrated in vacuo to yield a gummy solid which was dissolved in 1500 ml. of absolute alcohol. Crude hydrobromide salt (379 g.) crystallized on chilling and was recovered by filtration. Purified 4-picolylbromide hydrobromide (33.1 g., m.p. 187.5°-189° C.) was obtained by recrystallization of 50 g. of crude from absolute alcohol.

We claim:

1. A compound of the formula

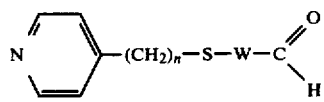

or

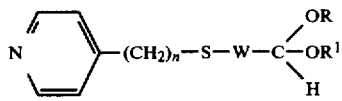

wherein
n is 1 or 2;
W is methylene, unsubstituted or substituted with either methyl or phenyl;

R and R¹ when taken separately are the same and are each $(C_1-C_4)$alkyl; and

R and R¹ when taken together are ethano or propano; or a pharmaceutically-acceptable acid addition salt thereof.

2. A compound of claim 1 wherein n is 1.

3. A compound of claim 2 wherein W is unsubstituted methylene.

4. The compound of claim 3 of the formula

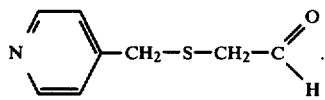

5. The compound of claim 3 of the formula

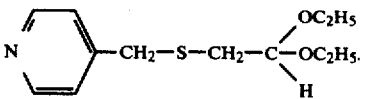

6. The compound of claim 3 of the formula

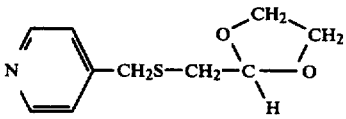

* * * * *